United States Patent
Fishman et al.

(10) Patent No.: US 11,464,963 B1
(45) Date of Patent: Oct. 11, 2022

(54) NITINOL BRAID PROCESSING PROCEDURE

(71) Applicant: Abiomed, Inc., Danvers, MA (US)

(72) Inventors: Robert Fishman, Danvers, MA (US); Mithun Rajaram, Danvers, MA (US); Emmanuel Ilongo, Danvers, MA (US); Vladimir Gilman, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 557 days.

(21) Appl. No.: 16/552,751

(22) Filed: Aug. 27, 2019

Related U.S. Application Data

(60) Provisional application No. 62/723,077, filed on Aug. 27, 2018.

(51) Int. Cl.
G08B 21/04 (2006.01)
A61M 60/135 (2021.01)

(52) U.S. Cl.
CPC ... *A61M 60/135* (2021.01); *A61M 2205/3368* (2013.01); *A61M 2207/00* (2013.01)

(58) Field of Classification Search
USPC ......... 340/539.12, 539.23, 539.27, 588, 596, 340/612, 622, 636.18, 640, 655, 686.6, 340/825.23
See application file for complete search history.

(56) References Cited

U.S. PATENT DOCUMENTS

| | | | |
|---|---|---|---|
| 4,699,611 A | 10/1987 | Bowden | |
| 5,139,486 A | 8/1992 | Moss | |
| 5,234,425 A | 8/1993 | Fogarty et al. | |
| 5,304,142 A | 4/1994 | Liebl et al. | |
| 5,320,611 A | 6/1994 | Bonutti et al. | |
| 5,395,341 A | 3/1995 | Slater | |
| 5,397,310 A | 3/1995 | Chu et al. | |
| 5,407,430 A | 4/1995 | Peters | |
| 5,488,960 A | 2/1996 | Toner | |
| 5,492,530 A | 2/1996 | Fischell et al. | |
| 5,536,255 A | 7/1996 | Moss | |
| 5,573,517 A | 11/1996 | Bonutti et al. | |
| 5,653,697 A | 8/1997 | Quiachon et al. | |
| 5,911,702 A | 6/1999 | Romley et al. | |
| 5,935,122 A | 8/1999 | Fourkas et al. | |

(Continued)

FOREIGN PATENT DOCUMENTS

EP  2995268 A1  3/2016

OTHER PUBLICATIONS

International Search Report and Written Opinion for Application No. PCT/US2019/018275 dated Jul. 15, 2019.

(Continued)

*Primary Examiner* — Daniel Previl
(74) *Attorney, Agent, or Firm* — Botos Churchill IP Law LLP

(57) ABSTRACT

Systems and methods for packaging an optical sensor assembly. An optical sensor assembly for use in a blood pump assembly comprises a visor affixed to a pump housing of the blood pump assembly. A support jacket is in contact with an inner surface of the visor, and defines a cavity in which an optical sensor is disposed. Silicone gel is introduced into the cavity, where it cures. Silicone gel within the cavity protects the optical sensor, and the support jacket prevents the overflowing of the gel and contamination of the visor.

20 Claims, 3 Drawing Sheets

(56) References Cited

U.S. PATENT DOCUMENTS

| | | |
|---|---|---|
| 5,971,993 A | 10/1999 | Hussein et al. |
| 5,997,562 A * | 12/1999 | Zadno-Azizi ..... A61M 25/0662 606/108 |
| 6,197,016 B1 | 3/2001 | Fourkas et al. |
| 6,338,730 B1 | 1/2002 | Bonutti et al. |
| 6,428,556 B1 | 8/2002 | Chin |
| 6,613,038 B2 | 9/2003 | Bonutti et al. |
| 6,692,462 B2 | 2/2004 | Mackenzie et al. |
| 6,814,715 B2 | 11/2004 | Bonutti et al. |
| 7,025,746 B2 | 4/2006 | Tal |
| 7,722,567 B2 | 5/2010 | Tal |
| 8,597,277 B2 | 12/2013 | Lenker et al. |
| 8,672,888 B2 | 3/2014 | Tal |
| 8,758,402 B2 | 6/2014 | Jenson et al. |
| 2003/0014068 A1 | 1/2003 | Bonutti et al. |
| 2005/0149105 A1 | 7/2005 | Leeflang et al. |
| 2006/0135981 A1 | 6/2006 | Lenker et al. |
| 2006/0287574 A1 | 12/2006 | Chin |
| 2007/0144731 A1 * | 6/2007 | Murray ................ E21B 23/04 166/120 |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2009/0240202 A1 | 9/2009 | Drasler et al. |
| 2010/0051182 A1 * | 3/2010 | Graham .................. B29C 70/56 156/425 |
| 2012/0022617 A1 * | 1/2012 | Tockman ............ A61N 1/36114 607/72 |
| 2013/0000551 A1 * | 1/2013 | Guignon ................ B29C 48/15 118/600 |
| 2013/0131718 A1 | 5/2013 | Jenson et al. |
| 2013/0317438 A1 | 11/2013 | Ellingwood et al. |
| 2013/0317481 A1 | 11/2013 | Ellingwood et al. |
| 2014/0173878 A1 * | 6/2014 | Merk ........................ A61F 2/95 29/446 |
| 2016/0066948 A1 | 3/2016 | Ellingwood et al. |
| 2016/0074011 A1 * | 3/2016 | Johnson .................... A61F 2/01 600/424 |
| 2016/0220358 A1 | 8/2016 | Wilson et al. |
| 2016/0354583 A1 | 12/2016 | Ellingwood et al. |
| 2017/0056063 A1 | 3/2017 | Ellingwood et al. |
| 2017/0281908 A1 | 10/2017 | Ellingwood et al. |
| 2018/0055637 A1 * | 3/2018 | von Oepen ...... A61B 17/00234 |

OTHER PUBLICATIONS

International Search Report and Written Opinion for application No. PCT/US2019/046543 dated Jan. 10, 2020.

* cited by examiner

102 — Forming a Sheath Assembly

104 — Placing the Sheath Assembly onto a Mandrel

106 — Placing a Second Sleeve Over the Tip of the Mandrel

108 — Sliding the First Sleeve So that the Proximal Edge of the Second Sleeve is Covered by a Distal End of the First Sleeve and Placing a Third Sleeve on the Proximal End of the Mandrel

110 — Heating the Sheath Assembly and the Second and Third Sleeves So that the First, Second, and Third Material Partially Penetrate the Sheath Frame

112 — Heating the Second Sleeve and the Distal End of the First Sleeve So that the First Material and Second Material Completely Penetrate the Sheath Frame

114 — Heating the Distal End of the Third Sleeve and the Proximal Portion of the Sheath Assembly That Overlaps with the Distal End of the Third Sleeve

NITINOL BRAID PROCESSING PROCEDURE

CROSS-REFERENCE TO RELATED APPLICATIONS

This application claims priority to U.S. Patent Application No. 62/723,077, filed Aug. 27, 2018, the contents of which are herein incorporated by reference in their entirety. The application is related to U.S. patent application Ser. No. 16/540,922 filed Aug. 14, 2019, the contents of which are herein incorporated by reference in their entirety.

BACKGROUND

An intravascular blood pump assembly, such as an assembly with an intracardiac blood pump, may be introduced into the heart to deliver blood from the heart into an artery. Intravascular blood pumps can be introduced percutaneously during a cardiac procedure through the vascular system, such as by a catheterization procedure. Some blood pumps are designed to support the left side of the heart, where they pull blood from the left ventricle of the heart and expel the blood through a cannula into the aorta. Some blood pumps that support the left side of the heart are introduced by a catheterization procedure through the femoral artery, into the ascending aorta, across the aortic valve, and into the left ventricle. Some systems are designed to support the right side of the heart, where the blood pump is introduced through a vein and into the right side of the heart through the venous system (i.e., the vena cava). Blood pump systems may also be surgically implanted or inserted through the subclavian and/or carotid arteries.

In one common approach, an intravascular blood pump assembly is inserted by a catheterization procedure through the femoral artery using a sheath, such as an expandable sheath. The expandable sheath may be sized to fit into the vasculature of the patient in an unexpanded state. The sheath may then expand to allow the passage of a blood pump or other medical device through the sheath, the blood pump or other medical device having a diameter that is larger than the diameter of the sheath in the unexpanded state. After the passage of the blood pump or other medical device through the sheath, the sheath may then return to the unexpanded state. Due to the flexibility of an expandable sheath, the forces exerted on a sheath as the sheath navigates the vasculature of a patient may cause the sheath to buckle or kink. Existing expandable sheaths comprise sheath frames containing a polymer coating. The coating may be applied to the sheath in order to prevent such buckling or kinking.

Manufacturing challenges exist in ensuring that a coating can be expeditiously applied to a sheath frame such that the coating is even along the length of the sheath frame, without compromising the ability of the sheath to expand, and without increasing the tendency of the sheath to kink or buckle under pressure. An additional manufacturing challenge is ensuring the desired degree of adhesion between the sheath frame and the coating of the sheath frame. Thus, it is desirable to design a manufacturing process for a coated expandable sheath that ensures the desired degree of adhesion between the sheath frame and the coating, without slowing the manufacturing process and without comprising the ability of the sheath to expand or resist kinking and buckling.

SUMMARY

The systems, methods, and devices described herein provide a method for manufacturing an expandable sheath for use in an intravascular blood pump system (or other blood pump systems). Such blood pump systems may be an Impella® pump. The sheath assemblies described herein are expandable, allowing for the introduction of the assemblies into the narrow vasculature of patient, while being able to accommodate pump system elements having larger diameters. The blood pump may have a rotor inside a pump housing, a cannula that receives blood being pumped through the system, a delivery mechanism (such as a catheter or surgical delivery set) for inserting the pump in the patient, and a drive unit for powering the pump. The drive unit may be an external motor and an electrical connection. Alternatively, the drive unit may be a mechanical cable connecting the rotor to an external motor. The cannula extends distal of the pump, and may include a flexible, atraumatic projection extending distal of the cannula.

The expandable sheath for use in an intravascular blood pump generally comprises a sheath frame surrounded by one or more sleeves. The frame may comprise at least one of a braid, a wound wire, and a laser-cut material. The sheath frame may comprise a metal. The metal may be at least one of Nitinol and stainless steel. The sleeves may comprise one or more plastics. The plastics may comprise at least one of TPU and polyether. The expandable sheath is manufactured by surrounding the sheath frame with the sleeves, and heating the sleeves and the frame around a mandrel. The frame and sleeves are heated in multiple steps, along multiple areas of the sheath, and to different temperatures and for different time periods. In general, the materials of the expandable sheath are heated at least twice, allowing the sheath frame to remain radially expandable while also remaining kink-resistant due to the various degrees of mobility that penetration of the sheath frame by the sleeve to variable depth achieves. The temperatures at which the sheath is heated, and the time periods over which the sheath is heated, are selected such that after heating, the materials of the plastic sleeves penetrate the sheath frame to various depths. The penetration of the sheath frame to various depths by the sleeves along its length provides the sheath with increased structural integrity, preventing the sheath from buckling or kinking upon insertion of the sheath into a patient.

In some implementations, the method for manufacturing an intravascular sheath comprises first forming a sheath assembly by placing a sheath frame into a first sleeve. The first sleeve comprises a first material having a first melting temperature. The sheath assembly is then placed onto the proximal end of a mandrel having a tapered distal tip. The sheath assembly is placed on the mandrel such that the sheath assembly covers at least the proximal end of the mandrel. A second sleeve is then placed over the tapered distal of the mandrel such that the proximal end of the second sleeve lies on the tapered distal tip of the mandrel. The second sleeve comprises a second material having a second melting temperature.

Subsequently, the first sleeve is moved in a distal direction relative to the sheath frame so that the proximal end of the second sleeve overlaps with the distal end of the first sleeve. In some implementations, the proximal end of the second sleeve is covered by the distal end of the first sleeve. In other implementations, the distal end of the first sleeve is covered by the proximal end of the second sleeve. The sheath assembly and the second sleeve are then heated around the mandrel for a first time period and at a first temperature. The first time period and the first temperature are set such that after the first time period, the first material and the second material penetrate the sheath frame to a first depth. The first temperature is also selected such that it is less than the first melting temperature. In certain implementations, the first depth is between about one-quarter of the width of the braid comprising the sheath frame and about three-quarters of the width of the braid comprising the sheath frame. In further implementations, the first depth is between about one-half of the width of the braid comprising the sheath frame and about two-thirds of the width of the braid comprising the sheath frame. In implementations wherein the first depth is not the entire width of the braid comprising the sheath frame, (i.e., as in implementations wherein the first depth is one-half of the width of the braid comprising the sheath frame), the sheath frame is said to be partially penetrated. Partial penetration of the sheath frame by the first material and the second material to the first depth advantageously provides the sheath assembly with increased structural integrity, reducing the likelihood of buckling while still allowing the sheath frame the flexibility required to expand in order to accommodate pump elements having a larger diameter than the sheath frame.

In the final step of the method, the second sleeve and the distal end of the first sleeve are heated around the mandrel for a second time period and at a second temperature to form the intravascular sheath. The second temperature and the second time period are set such that after the second time period, the first material in the distal end of the first sleeve and the second material penetrate the sheath frame to a second depth. Similarly to the first temperature, the second temperature is set such that the first material is heated below the first melting temperature, and such that the second material is heated below the second melting temperature. In some implementations, the second depth is the complete width of the braid comprising the sheath frame. In implementations wherein the second depth is the complete width of the braid comprising the sheath frame, the sheath frame is said to be completely penetrated. The penetration of the distal end of the sheath frame by the first and second materials causes the first sleeve and the second sleeve to flow together and provides the advantage of preventing the terminating ends of the wires comprising the sheath frame from extruding from the sleeves. The heating of the distal end of the sheath assembles configures the terminating ends of the wires comprising the sheath frame to be completely encapsulated in polymer. This may prevent damage that may otherwise be caused by having exposed wires protruding from the sheath. Further, the coating of the sheath frame may increase the kink resistance of the sheath frame. At least one advantage of the resistance to kinking of the sheath frame is the ability of the sheath to navigate through tortuous segments of the vasculature and also for procedures wherein the blood vessel is deep relative to the insertion site of the device.

In certain implementations, the first temperature at which the sheath assembly and the second sleeve are heated is less than the second temperature at which the second sleeve and the distal end of the first sleeve are heated. In further implementations, the first temperature is less than at least one of the first melting temperature and the second melting temperature. In certain implementations, the first temperature is less than both the first melting temperature and the second melting temperature. In some implementations, the second temperature is less than at least one of the first melting temperature and the second melting temperature. In certain implementations, the second temperature is less than both the first melting temperature and the second melting temperature. In further implementations, the first melting temperature and the second melting temperature are substantially the same. In certain implementations of the method, the second sleeve and the distal end of the first sleeve are heated around the mandrel for the second time period and at the second temperature before the sheath assembly and the second sleeve are heated around the mandrel for the first time period at the first temperature.

The heating of the first material and of the second material increases a first tackiness of the first material and a second tackiness of the second material. In some implementations, the first tackiness is greater than the second tackiness. In other implementations, the second tackiness is greater than the first tackiness. In certain implementations, the first tackiness and the second tackiness are substantially the same. The relationships between the first temperature, the second temperature, the first melting temperature, and the second melting temperature can be selected such that the first material and the second material, after heating, exhibit a first tackiness and a second tackiness, respectively, that allow for the desired adhesion of the first material and the second material to the sheath frame. It is this desired adhesion, coupled with the selection of the first depth and the second depth, that advantageously provides the sheath frame with the desired degrees of penetration along its length. For example, the first temperature, the second temperature, the first melting temperature, and the second melting temperature can be selected such that the proximal portion of the sheath frame is partially penetrated by the first material and the second material, and such that the distal tip of the sheath is completely penetrated by the first material and the second material.

In some implementations, the first depth is less than the second depth. In further implementations, the penetration of the sheath frame to the first depth by the first material and the second material coats the sheath frame while advantageously allowing the sheath frame to expand. In certain implementations, the intravascular sheath is radially expandable.

In some implementations, the first temperature is between about 100 degrees Celsius and about 180 degrees Celsius. In certain implementations, the first temperature is between about 120 degrees Celsius and about 160 degrees Celsius. In further implementations, the first temperature is about 140 degrees Celsius.

In some implementations, the first time period is between about 1 minute and about 3 minutes. In certain implementations, the first time period is about 2 minutes.

In some implementations, the second temperature is between about 110 degrees Celsius and about 190 degrees Celsius. In certain implementations, the second temperature is between about 130 degrees Celsius and about 170 degrees Celsius. In further implementations, the second temperature is about 150 degrees Celsius.

In some implementations, the second time period is between about 1 minute and about 3 minutes. In further implementations, the second time period is about 2 minutes. As with the relationship between the first temperature, the second temperature, the first melting temperature, and the second melting temperature, the first time period and the second time period may be selected such that the first heating and the second heating cause the first material and the second material to exhibit a desired first tackiness and a desired second tackiness. Such tackinesses provide the first material and the second material with a desired adhesion to the sheath frame. The appropriate adhesion, coupled with the desired first depth and second depth, provides the sheath with a sufficient coating without harming the ability of the sheath to expand, allowing the sheath to withstand forces that would otherwise lead the sheath to buckle upon insertion of the sheath into a patient without compromising the ability of the sheath to expand to accommodate pump elements having larger diameters than the sheath in an unexpanded state.

In some implementations, the proximal end of the second sleeve abuts a distal end of the proximal end of the mandrel. In certain implementations, the proximal end of the mandrel is cylindrical. In such implementations, the mandrel may have a circular cross-section. In other implementations, the cylindrical mandrel may have an elliptical cross-section. The cross-section of the mandrel, in other implementations, is a polygon. In further implementations, the cross-section of the mandrel may be a free-form shape. Generally, the mandrel may comprise any geometry that allows for the sheath assembly and other components to be placed around the mandrel and heated. In certain implementations, the sheath may have a circular cross-section. In further implementations, the sheath may have an elliptical cross-section. The sheath may be configured to change in cross-section after the introduction of pump elements through the sheath. The variation in cross-section of an expandable sheath of a given perimeter or circumference advantageously allows for the simultaneous introduction of devices using a hub into the sheath that having large diameters. For example, an expandable sheath having a variable cross-section that is able to accommodate both a blood pump and a catheter could be employed for percutaneous coronary intervention. Such sheaths allow for dual access of devices by optimizing the space available within the introducer sheath.

Additionally, such implementations involving variable cross-section expandable sheaths allow for a free shape (i.e., a shape of the expandable sheath within the vasculature of the patient and not containing a device) having a small diameter for insertion into the arteriotomy. This allows the arteriotomy to be kept small, as the width of the sheath is aligned with the formation of the resulting arteriotomy. An elliptical cross-section can also be used for insertion into the arteriotomy, while keeping the arteriotomy small. The elliptical cross-section helps to obtain distal flow, as the elliptical cross-section generally matches the shape of the arteriotomy. Additionally, the incorporation of a small, variable diameter expandable sheath improves hemostasis during procedures. The forces exerted on the vasculature by the sheath in implementations wherein the expandable sheath has a small diameter free shape mimic the way in which blood vessels naturally stretch, advantageously preventing damage unto the vasculature by the sheath.

The first material and the second material may, in general, comprise a polymer. In certain implementations, the first material and second material comprise at least one of polyurethane and polyether. In some implementations, the first material and the second material are the same. The desired polymers that the first material and the second material comprise may be selected based on their respective melting temperatures. As such, the first material, the second material, the first temperature, the second temperature, the first time period, and the second time period may be selected in order to create the desired adhesion and penetration depth between the first material, the second material, and the sheath frame. Penetration of the sheath frame by the first material and the second material to the first depth advantageously provides the sheath with a polymer coating while allowing the sheath to expand in order to accommodate pump elements having larger diameters than the sheath in an unexpanded state. The coating of the sheath frame further allows the sheath to resist kinking upon insertion of the sheath assembly into the patient.

In further implementations, the sheath frame comprises a metal. In certain implementations, the metal comprises at least one of stainless steel and Nitinol. The metal is selected in order to provide a given adhesion between the sheath frame, the first material, and the second material, as well as to provide the sheath frame with the ability to withstand buckling upon insertion into the vasculature of that patient while also allowing the sheath frame to expand. In some implementations, the intravascular sheath is used for the percutaneous insertion of an intravascular blood pump into a patient. In such implementations, the metal selected for use in the sheath frame must allow the sheath frame to expand in order to accommodate the widest elements of the intravascular blood pump.

In some implementations, a method for manufacturing an intravascular sheath comprises forming a sheath assembly by placing a sheath frame into a first sleeve. The first sleeve in such implementations comprises a first material having a first melting temperature. The sheath assembly is then placed onto a mandrel.

In some implementations, the mandrel comprises a proximal section having a first length and a first diameter. In some implementations, the first length is between about 10 millimeters and about 20 millimeters. In certain implementations, the first length is between about 12 millimeters and about 18 millimeters. In further implementations, the first length is between about 14 millimeters and about 16 millimeters. In some implementations, the first length is about 15 millimeters. In some implementations, the first diameter is between about 2 Fr and about 6 Fr. In certain implementations, the first diameter is between about 3 Fr and about 5 Fr. In further implementations, the first diameter is about 4 Fr.

In certain implementations, the mandrel further comprises a first transition region disposed distal of the proximal section. The first transition region is characterized in that the diameter of the first transition region varies over the length of the first transition region, from the proximal end of the first transition region to the distal end of the first transition region. In certain implementations, the variation in diameter is uniform along the length of the first transition region (i.e., the diameter changes at a constant rate along the length of the first transition region). In other implementations, the variation in diameter is non-uniform along the length of the first transition region. The diameter of the first transition region at the proximal end of the first transition region is equal to the first diameter. In some implementations, the diameter of the first transition region decreases from the first diameter at the proximal end of the first transition region to about one-half of the first diameter at the distal end of the first transition region. In certain implementations, the diameter of the first transition region decreases from the first diameter at the proximal end of the first transition region to about three-quarters of the first diameter at the distal end of the first transition region. In other implementations, the diameter of the first transition region increases from the first diameter at the proximal end of the first transition region to about 1.5 times the first diameter at the distal end of the first transition region. In certain implementations, the diameter of the first transition region increases from the first diameter at the proximal end of the first transition region to about 1.25 times the first diameter at the distal end of the first transition region. In certain implementations, the length of the first transition region is between about 5 millimeters and about 15 millimeters. In further implementations, the length of the first transition region is between about 7 millimeters and about 13 millimeters. In certain implementations, the length of the first transition region is between about 9 millimeters and about 11 millimeters. In further implementations, the length of the first transition region is about 10 millimeters.

In further implementations, the mandrel further comprises a medial section disposed distal of the first transition region. The medial section comprises a second length and a second diameter. The diameter of the first transition region at the distal end of the first transition region is equal to the second diameter. In some implementations, the second length is between about 10 millimeters and about 20 millimeters. In certain implementations, the second length is between about 12 millimeters and about 18 millimeters. In further implementations, the second length is between about 14 millimeters and about 16 millimeters. In some implementations, the second length is about 15 millimeters. In some implementations, the second diameter is between about 2 Fr and about 6 Fr. In certain implementations, the second diameter is between about 3 Fr and about 5 Fr. In further implementations, the second diameter is about 4 Fr.

In some implementations, the mandrel further comprises a second transition region disposed distal of the medial section. Similarly to the first transition region, the second transition region is characterized in that the diameter of the second transition region varies over the length of the second transition region, from the proximal end of the second transition region to the distal end of the second transition region. In certain implementations, the variation in diameter is uniform along the length of the second transition region. In other implementations, the variation in diameter is non-uniform along the length of the second transition region. In some implementations, the variation in diameter of the second transition region is equal to the variation in diameter of the first transition region. In other implementations, the variation in diameter of the second transition region is not equal to the variation in diameter of the first transition region. The diameter of the second transition region at the proximal end of the second transition region is equal to the second diameter. In some implementations, the diameter of the second transition region decreases from the second diameter at the proximal end of the second transition region to about one-half of the second diameter at the distal end of the second transition region. In certain implementations, the diameter of the second transition region decreases from the second diameter at the proximal end of the second transition region to about three-quarters of the second diameter at the distal end of the second transition region. In other implementations, the diameter of the second transition region increases from the second diameter at the proximal end of the second transition region to about 1.5 times the second diameter at the distal end of the second transition region. In certain implementations, the diameter of the second transition region increases from the second diameter at the proximal end of the second transition region to about 1.25 times the second diameter at the distal end of the second transition region. In certain implementations, the length of the second transition region is between about 5 millimeters and about 15 millimeters. In further implementations, the length of the second transition region is between about 7 millimeters and about 13 millimeters. In certain implementations, the length of the second transition region is between about 9 millimeters and about 11 millimeters. In further implementations, the length of the second transition region is about 10 millimeters.

In further implementations, the mandrel further comprises a distal section disposed distal of the second transition region, and having a third length and a third diameter. The diameter of the second transition region at the distal end of the second transition region is equal to the third diameter. In some implementations, the third length is between about 10 millimeters and about 20 millimeters. In certain implementations, the third length is between about 12 millimeters and about 18 millimeters. In further implementations, the third length is between about 14 millimeters and about 16 millimeters. In some implementations, the third length is about 15 millimeters. In some implementations, the third diameter is between about 2 Fr and about 6 Fr. In certain implementations, the third diameter is between about 3 Fr and about 5 Fr. In further implementations, the third diameter is about 4 Fr.

In certain implementations, the sheath assembly is placed onto the mandrel so that the distal end of the sheath assembly terminates in the second transition region, and so that the proximal end of the sheath assembly terminates in the first transition region. In some implementations, the proximal end of the sheath assembly terminates within the proximal section of the mandrel. In further implementations, the method comprises subsequently placing a second sleeve onto the second transition region of the mandrel such that a proximal end of the second sleeve terminates within the second transition region. In some implementations, the second sleeve comprises a second material having a second melting temperature. In certain implementations, the first sleeve is moved along the sheath frame in a distal direction so that the proximal end of the second sleeve overlaps with a distal end of the first sleeve. In some implementations, the distal end of the first sleeve covers the proximal end of the second sleeve. In other implementations, the proximal end of the second sleeve covers the distal end of the first sleeve.

In some implementations, the method further comprises placing a third sleeve on the proximal section of the mandrel such that a distal end of the third sleeve terminates within the proximal section of the mandrel and overlaps with a proximal portion of the sheath assembly. In certain implementations, the third sleeve comprises a third material having a third melting temperature.

In certain implementations, the method further comprises heating the sheath assembly, the second sleeve, and the third sleeve around the mandrel for a first time period and at a first temperature. The first time period and the first temperature may be set such that after the first time period, the first material, the second material, and the third material penetrate the sheath frame to a first depth. In certain implementations, the first depth is between about one-half the width of the braid comprising the sheath frame and about two-thirds the width of the braid comprising the sheath frame. As previously discussed, in implementations wherein the first depth is not the complete width of the braid comprising the sheath frame (i.e., in implementations wherein the first depth is one-half of the width of the braid comprising the sheath frame), the sheath frame is said to be partially penetrated. Partial penetration of the sheath frame by the first material and the second material to the first depth coats the sheath frame, such a coating advantageously providing the sheath assembly with increased structural integrity, reducing the likelihood of buckling while still allowing the sheath frame the flexibility required to expand in order to accommodate intravascular blood pump elements having a larger diameter than the sheath frame.

In further implementations, the method comprises heating the distal end of the sheath assembly and the second sleeve around the mandrel for a second time period and at a second temperature. The second time period and the second temperature may be set such that after the second time period, the first material and the second material completely penetrate the sheath frame to a second depth. As discussed above, in some implementations, the second depth is the complete width of the braid comprising the sheath frame. In implementations wherein the second-depth is the complete width of the braid comprising the sheath frame, the sheath frame is said to be completely penetrated. Complete penetration of the sheath frame by the first material and the second material in the area of the tapered distal tip of the mandrel allows the tip of the sheath frame to remain resistant to kinking or buckling upon the insertion of the device into the vasculature of a patient. This feature is particularly advantageous both for procedures involving the navigation of the sheath frame through tortuous segments of the vasculature and also for procedures wherein the blood vessel is deep relative to the insertion site of the device. Further, the heating of the distal end of the sheath assembly and of the second sleeve coats the distal end of the sheath frame by causing the first sleeve and the second sleeve to flow together in order to advantageously prevent damage due to the extrusion of wires from the distal end of the intravascular sheath.

In further implementations, the method additionally comprises heating the distal end of the third sleeve and the proximal portion of the sheath assembly that overlaps with the distal end of the third sleeve around the mandrel for a third time period and at a third temperature to form the intravascular sheath. In some implementations, the third temperature and the third time period are set such that after the third time period, the first material and the third material penetrate the sheath frame to a third depth. Additionally, the third temperature is set such that the first material and the third material are heated below the first melting temperature and below a third melting temperature temperature, respectively. Subsequently, the mandrel is removed from the intravascular sheath. In certain implementations, the first depth is less than the second depth and the third depth. In further implementations, the second depth and the third depth are substantially the same. In some implementations, the third depth is less than the first depth and the second depth. In other implementations, the first depth and the third depth are substantially the same. In some implementations, the intravascular sheath is radially expandable. The first depth, second depth, and third depth must therefore be selected such that the sheath maintains its ability to expand in order to accommodate elements of an intravascular blood pump.

In some implementations, heating the first material, the second material, and the third material increases a first tackiness of the first material, a second tackiness of the second material, and a third tackiness of the third material. In some implementations, the first tackiness is greater than at least one of the second tackiness and the third tackiness. In further implementations, the first tackiness is greater than both the second tackiness and the third tackiness. In other implementations, the second tackiness is greater than at least one of the first tackiness and the third tackiness. In other implementations, the third tackiness is greater than at least one of the first tackiness and the second tackiness. In certain implementations, the first tackiness, the second tackiness, and the third tackiness are substantially the same. In other implementations, none of the first tackiness, the second tackiness, and the third tackiness are substantially the same. The relationships between the first temperature, the second temperature, the third temperature, the first melting temperature, the second melting temperature, and the third melting temperature can be selected such that the first material, the second material, and the third material, after heating, exhibit a first tackiness, a second tackiness, and a third tackiness, respectively, that allow for the desired adhesion of the first material, the second material, and the third material to the sheath frame. It is this desired adhesion, coupled with the selection of the first depth, the second depth, and the third depth that advantageously provides the sheath frame with the desired degrees of penetration along its length. The variable penetration of the sheath frame by the first material, the second material, and the third material in turns provides the sheath frame, and thus, the intravascular sheath, with the desired mechanical properties including resistance to kinking and ability to expand.

In general, the order in which the elements of the intravascular sheath are heated may be selected to expedite manufacturing. In certain implementations, the distal end of the sheath assembly and the second sleeve are heated around the mandrel for the second time period and at the second temperature before the sheath assembly, the second sleeve, and the third sleeve are heated for the first time period at and at the first temperature. In further implementations, the distal end of the third sleeve and the proximal portion of the sheath assembly that overlaps with the distal end of the third sleeve are heated for the third time period and at the third temperature before the sheath assembly, the second sleeve, and the third sleeve are heated for the first of time and at the first temperature. In some implementations, the distal end of the third sleeve and the proximal portion of the sheath assembly that overlaps with the distal end of the third sleeve are heated for the third time period and at the third temperature before the distal end of the sheath assembly and the second sleeve are heated around the mandrel for the second time period and at the second temperature. In certain implementations, the heating of the distal end of the sheath assembly and the second sleeve (i.e., heating the elements of the intravascular sheath around the second transition portion of the mandrel) comprises heat-shrinking the distal end of the sheath assembly and the second sleeve. In further implementations, the heat-shrinking of the distal end of the sheath assembly and the second sleeve is performed using a TPFE heat shrink.

In certain implementations, the first temperature is less than at least one of the second temperature and the third temperature. In some implementations, the first temperature is less than both the second temperature and the third temperature. In certain implementations, the first temperature is less than at least one of the first melting temperature, the second melting temperature, and the third melting temperature.

In further implementations, the second temperature is less than at least one of the first melting temperature and the second melting temperature. In some implementations, the third temperature is less than at least one of the first melting temperature and the third melting temperature. In certain implementations, the first melting temperature, the second melting temperature, and the third melting temperature are substantially the same. In other implementations, only two of the first melting temperature, the second melting temperature, and the third melting temperature are substantially the same. In further implementations, none of the first melting temperature, the second melting temperature, and the third melting temperature are substantially the same.

In some implementations, the first temperature is between about 100 degrees Celsius and about 180 degrees Celsius. In certain implementations, the first temperature is between about 120 degrees Celsius and about 160 degrees Celsius. In further implementations, the first temperature is about 140 degrees Celsius.

In some implementations, the second temperature is between about 110 degrees Celsius and about 190 degrees Celsius. In certain implementations, the second temperature is between about 130 degrees Celsius and about 170 degrees Celsius. In further implementations, the second temperature is about 150 degrees Celsius.

In some implementations, the third temperature is between about 110 degrees Celsius and about 190 degrees Celsius. In certain implementations, the third temperature is between about 130 degrees Celsius and about 170 degrees Celsius. In further implementations, the third temperature is about 150 degrees Celsius.

In some implementations, the first time period is between about 1 minute and about 3 minutes. In certain implementations, the first time period is about 2 minutes.

In some implementations, the second time period is between about 1 minute and about 3 minutes. In further implementations, the second time period is about 2 minutes.

In some implementations, the third time period is between about 1 minute and about 3 minutes. In further implementations, the third time period is about 2 minutes.

In certain implementations, the proximal end of the mandrel is cylindrical. In some implementations, the proximal end of the second sleeve abuts a distal end of the proximal end of the mandrel.

In some implementations, the first length is between about one time and about 6 times at least one of the second length and the third length. In certain implementations, the first length is between about 3 times and about 4 times at least one of the second length and the third length. In some implementations, the second length is between about one time and about 6 times at least one of the first length and the third length. In certain implementations, the second length is between about 3 times and about 4 times at least one of the first length and the third length. In some implementations, the third length is between about one time and about 6 times at least one of the first length and the second length. In certain implementations, the third length is between about 3 times and about 4 times at least one of the first length and the second length. In some implementations, the first length is equal to at least one of the second length and the third length. In further implementations, the first length is equal to both the second length and the third length. In certain implementations, the second length is equal to at least one of the first length and the third length. In other implementations, none of the first length, the second length, and the third length are equal.

In certain implementations, the first diameter is between about one time and about 6 times at least one of the second diameter and the third diameter. In further implementations, the first diameter is between about 3 times and about 4 times at least one of the second diameter and the third diameter. In some implementations, the second diameter is between about one time and about 6 times at least one of the first diameter and the third diameter. In further implementations, the second diameter is between about 3 times and about 4 times at least one of the first diameter and the third diameter. In certain implementations, the third diameter is between about one time and about 6 times at least one of the first diameter and the second diameter. In further implementations, the third diameter is between about 3 times and about 4 times at least one of the first diameter and the second diameter. In certain implementations, the first diameter is equal to at least one of the second diameter and the third diameter. In further implementations, the first length is equal to both the second diameter and the third diameter. In certain implementations, the second diameter is equal to at least one of the first diameter and the third diameter. In other implementations, none of the first diameter, the second diameter, and the third diameter are equal. In some implementations, the transition regions of the mandrel are tapered regions having variable diameters.

In further implementations, the proximal end of the mandrel is cylindrical. In some implementations, the proximal end of the second sleeve abuts a distal end of the medial section. In some implementations, the first material, the second material, and the third material comprise at least one of polyurethane and polyether. In further implementations, at least two of the first material, the second material, and the third material are the same. In some implementations, the sheath frame comprises a metal. In certain implementations, the metal comprises at least one of stainless steel and Nitinol. In further implementations, the mandrel is removed from the intravascular sheath in the proximal direction. In some implementations, the intravascular sheath is used for the percutaneous insertion of an intravascular blood pump.

In some implementations, a method for manufacturing an intravascular sheath comprises forming a sheath assembly by placing a sheath frame into a first sleeve. The method further comprises sliding the sheath assembly onto a proximal cylindrical end of a mandrel, the mandrel having a distal tapered tip, such that the sheath assembly covers the proximal cylindrical end of the mandrel. In certain implementations, the method additionally comprises placing a second sleeve over the distal tapered tip of the mandrel such that a proximal end of the second sleeve abuts a distal end of the proximal cylindrical end of the mandrel. In further implementations, the method then comprises advancing the first sleeve over the distal tapered tip of the mandrel such that the first sleeve covers the proximal end of the second sleeve. In further implementations, the sheath assembly and the second sleeve are then heated with a first heating load to form a coated sheath assembly. In some implementations, the coated sheath assembly is then heat-shrunk with a second heating load.

BRIEF DESCRIPTION OF THE FIGURES

The foregoing and other objects and advantages will be apparent upon consideration of the following detailed description, taken in conjunction with the accompanying drawings, in which like reference characters refer to like parts throughout, and in which:

FIG. 1 shows an illustrative method of manufacturing an intravascular sheath assembly;

DETAILED DESCRIPTION

Figure 2:
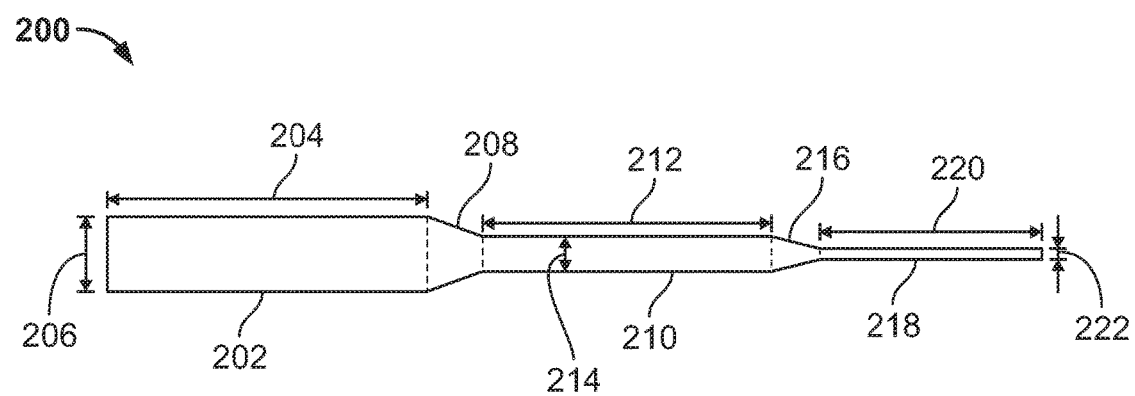
FIG. 2 shows a first illustrative mandrel.

To provide an overall understanding of the systems, method, and devices disclosed herein, certain illustrative implementations will be described. Although the implementations and features described herein are specifically described for use in connection with a blood pump assembly, it will be understood that the teaching may be adapted and applied to other pumps and other types of medical devices.

FIG. 1A shows an illustrative method 100 of manufacturing an intravascular sheath for use in the percutaneous insertion of a blood pump assembly. Method 100 of manufacturing an intravascular sheath first comprises step 102 of forming a sheath assembly. The sheath assembly comprises a sheath frame around which an operator of the method places a first sleeve. In some implementations, the sheath frame comprises a metal. In certain implementations, the metal comprises at least one of stainless steel and Nitinol. The first sleeve comprises a first material and has a first melting temperature. After forming the sheath assembly in step 102, the operator of the method then places the sheath assembly onto a mandrel in step 104. In some implementations, the mandrel comprises a proximal section having a first length and a first diameter, a first transition region disposed distal of the proximal section, a medial section having a second length and a second diameter disposed distal of the first transition region, a second transition region disposed distal of the medial section, and a distal section disposed distal of the second transition region and having a third length and a third diameter. In certain implementations the sheath assembly is placed onto the proximal end of a mandrel having a tapered distal tip. As discussed previously, the sheath assembly is placed on the mandrel such that the sheath assembly covers at least the proximal end of the mandrel. Step 106 then comprises placing a second sleeve over the tip of the mandrel. In certain implementations, the second sleeve is placed over the tapered distal tip of the mandrel such that the proximal end of the second sleeves lies on the tapered distal tip of the mandrel. The second sleeve comprises a second material having a second melting temperature. At least one advantage of the mandrel comprising different segments along is length is that the sections can be easily isolated for heating at different temperatures and over different time periods, allowing for the sheath frame to have various degrees of penetration by the sleeves along its length.

In some implementations, the first length is between about one time and about 6 times at least one of the second length and the third length. In certain implementations, the first length is between about 3 times and about 4 times at least one of the second length and the third length. In some implementations, the second length is between about one time and about 6 times at least one of the first length and the third length. In certain implementations, the second length is between about 3 times and about 4 times at least one of the first length and the third length. In some implementations, the third length is between about one time and about 6 times at least one of the first length and the second length. In certain implementations, the third length is between about 3 times and about 4 times at least one of the first length and the second length. In some implementations, the first length is equal to at least one of the second length and the third length. In further implementations, the first length is equal to both the second length and the third length. In certain implementations, the second length is equal to at least one of the first length and the third length. In other implementations, none of the first length, the second length, and the third length are equal. At least one advantage of the mandrel sections being configured to have a range of suitable lengths is that the dimensions of a given mandrel that used for manufacturing a sheath can be selected in order to create a sheath with dimensions that are appropriate for specific procedures. For example, mandrels with smaller overall lengths can be used to manufacture sheaths for use in pediatric operations, while larger mandrels can be used to manufacture sheaths for use in adult patients.

In certain implementations, the first diameter is between about one time and about 6 times at least one of the second diameter and the third diameter. In further implementations, the first diameter is between about 3 times and about 4 times at least one of the second diameter and the third diameter. In some implementations, the second diameter is between about one time and about 6 times at least one of the first diameter and the third diameter. In further implementations, the second diameter is between about 3 times and about 4 times at least one of the first diameter and the third diameter. In certain implementations, the third diameter is between about one time and about 6 times at least one of the first diameter and the second diameter. In further implementations, the third diameter is between about 3 times and about 4 times at least one of the first diameter and the second diameter. In certain implementations, the first diameter is equal to at least one of the second diameter and the third diameter. In further implementations, the first length is equal to both the second diameter and the third diameter. In certain implementations, the second diameter is equal to at least one of the first diameter and the third diameter. In other implementations, none of the first diameter, the second diameter, and the third diameter are equal. Similarly to the variable lengths of the sheath sections, at least one advantage of the mandrel sections being configured to have a range of suitable diameters is that the dimensions of a given mandrel that used for manufacturing a sheath can be selected in order to create a sheath with dimensions that are appropriate for specific procedures. For example, mandrels with smaller overall diameters can be used to manufacture sheaths for use in pediatric operations, while larger mandrels can be used to manufacture sheaths for use in adult patients.

After placing the second sleeve over the tip of the mandrel in step 106, the operator moves the first sleeve in the distal direction so that the proximal end of the second sleeve overlaps with the distal end of the first sleeve in step 108. In some implementations, the proximal end of the second sleeve covers the distal end of the first sleeve. In other implementations, the distal end of the first sleeve covers the proximal end of the second sleeve. Further, the operator places a third sleeve on the proximal end of the mandrel such that a distal end of the third sleeve overlaps with a proximal end of the first sleeve. In certain implementations, the second sleeve covers the distal end of the first sleeve and in other implementations, the distal end of the first sleeve covers the second sleeve. In step 110 of method 100, the sheath assembly and the second and third sleeves are then heated so that a first material of the first sleeve, a second material of the second sleeve, and a third material of the third sleeve penetrate the sheath frame to a first depth. In certain implementations, the first time period and the first temperature are set such that after the first time period, the first material and the second material penetrate the sheath frame to a first depth. In some implementations, the first depth is one-half the width of the braid comprising the sheath frame. In further implementations, the first depth is two-thirds the width of the braid comprising the frame. In implementations wherein the first depth is not the entire width of the braid comprising the sheath frame, the sheath frame is said to be partially penetrated. At least one advantage of the heating of the first and second materials is that the respective tackinesses of the materials also increase, allowing the materials to adhere sufficiently to the sheath frame, Penetration of the sheath frame by the first material, the second material, and the third material to the first depth advantageously coats the sheath frame. The first depth, second depth, and third depth are further selected such that the sheath maintains its ability to expand in order to accommodate elements of an intravascular blood pump. The coating of the sheath frame by the sleeve materials advantageously provides the sheath assembly with increased structural integrity, reducing the likelihood of buckling while still allowing the sheath frame the flexibility required to expand in order to accommodate pump elements having a larger diameter than the sheath frame.

In step 112 of method 100, the second sleeve and the distal end of the first sleeve are heated so that the first material and the second material penetrate the sheath frame to a second depth, and such that a first tackiness of the first material and a second tackiness of the second material are increased. Similarly to the first time period and first temperature, the second temperature and the second time period are set such that after the second time period, the first material in the distal end of the first sleeve and the second material penetrate the sheath frame to a second depth. In some implementations, the second depth is the complete width of the braid comprising the sheath frame. In implementations wherein the second-depth is the complete width of the braid comprising the sheath frame, the sheath frame is said to be completely penetrated. Complete penetration of the sheath frame by the first material and the second material in the area of the tapered distal tip of the mandrel allows the tip of the sheath frame remains resistant to kinking or buckling upon the insertion of the device into the vasculature of a patient. At least one advantage of the kink-resistance of the sheath is that the sheath can be utilized in procedures involving the navigation of the sheath frame through tortuous segments of the vasculature and also for procedures wherein the blood vessel is deep relative to the insertion site of the device. Additionally, the complete penetration of the distal tip by the first and second sleeves causes the first and second sleeves to flow together to coat the sheath frame, Equivalently, after heating the distal tip of the device, the terminating ends of the wires are fully encapsulated in polymer, preventing wires that would otherwise extrude from the distal tip of the intravascular sheath from causing damage to the patient.

In certain implementations, the first temperature is less than the second temperature. In further implementations, the first temperature is less than at least one of the first melting temperature and the second melting temperature. In certain implementations, the first temperature is less than both the first melting temperature and the second melting temperature. In some implementations, the second temperature is less than at least one of the first melting temperature and the second melting temperature. In certain implementations, the second temperature is less than both the first melting temperature and the second melting temperature. In further implementations, the first melting temperature and the second melting temperature are substantially the same. In certain implementations of the method, the second sleeve and the distal end of the first sleeve are heated around the mandrel for the second time period and at the second temperature before the sheath assembly and the second sleeve are heated around the mandrel for the first time period at the first temperature. At least one advantage of the configuration of the first and second temperatures to be below the first and second melting points, respectively, is that the first and second materials undergo an increase in tackiness upon heating without becoming liquefied by reaching their respective melting temperatures.

The heating of the first material and of the second material increases a first tackiness of the first material and a second tackiness of the second material, allowing for improved adhesion of the first material and of the second material to the sheath frame. In some implementations, the first tackiness is greater than the second tackiness. In other implementations, the second tackiness is greater than the first tackiness. In certain implementations, the first tackiness and the second tackiness are substantially the same. The relationships between the first temperature, the second temperature, the first melting temperature, and the second melting temperature can be selected such that the first material and the second material, after heating, exhibit a first tackiness and a second tackiness, respectively, that allow for the desired adhesion of the first material and the second material to the sheath frame. It is this desired adhesion, coupled with the selection of the first depth and the second depth, that advantageously provides the sheath frame with the desired degrees of penetration along its length. For example, the first temperature, the second temperature, the first melting temperature, and the second melting temperature can be selected such that the proximal portion of the sheath frame is partially penetrated by the first material and the second material, and such that the distal tip of the sheath is completely penetrated by the first material and the second material.

In certain implementations, the heating of the distal end of the sheath assembly and the second sleeve (i.e., heating the elements of the intravascular sheath around the second transition portion of the mandrel) comprises heat-shrinking the distal end of the sheath assembly and the second sleeve. In further implementations, the heat-shrinking of the distal end of the sheath assembly and the second sleeve is performed using a TPFE heat shrink. At least one advantage of the heat-shrinking of the distal end of the sheath assembly and the second sleeve is that the shape of the distal tip of the intravascular sheath can be adjusted to have a desired geometry based on the geometry of the heat-shrink used.

In some implementations, the method further comprises step 114 of heating the distal end of the third sleeve and the proximal portion of the sheath assembly that overlaps with the distal end of the third sleeve for a third time period and at a third temperature to form the intravascular sheath. Heating the distal end of the third sleeve and the proximal portion of the sheath assembly that overlaps with the distal end of the third sleeve increases a first tackiness of the first material and a third tackiness of the third material. At least one advantage of heating of the third sleeve and the proximal portion of the sheath assembly that overlaps with the distal end of the third sleeve is that the proximal portion of the sheath frame is configured to be penetrated by the first and third materials, allowing for a degree of flexibility of the proximal end of the portion consistent with the degree of penetration of the proximal portion of the sheath frame by the first and third materials. After the intravascular sheath is formed, the mandrel is removed. In some implementations, the mandrel is removed from the proximal end of the intravascular sheath. In other implementations, the mandrel is removed from the distal end of the intravascular sheath.

In certain implementations, the third temperature and the third time period are set such that after the third time period the first material and the third material penetrate the sheath frame to a third depth. The third temperature is additionally set such that the first material is heated below a first melting temperature and such that the third material is heated below a third melting temperature allowing the first material and the second material to exhibit the desired adhesion to the sheath frame by increasing their respective tackinesses. The increase in the first tackiness and in the third tackiness allows the first material and the third material, respectively, to more readily adhere to the sheath frame without becoming a liquid. It is this desired adhesion, coupled with the selection of the first depth, the second depth, and the third depth that advantageously provides the sheath frame with the desired degrees of penetration along its length. The variable penetration of the sheath frame by the first material, the second material, and the third material in turns provides the sheath frame, and thus, the intravascular sheath, with the desired mechanical properties including resistance to kinking and ability to expand.

In some implementations, the first temperature is between about 100 degrees Celsius and about 180 degrees Celsius. In certain implementations, the first temperature is between about 120 degrees Celsius and about 160 degrees Celsius. In further implementations, the first temperature is about 140 degrees Celsius. In some implementations, the first melting temperature is between about 120 degrees Celsius and about 200 degrees Celsius. In certain implementations, the first melting temperature is between about 140 degrees Celsius and about 180 degrees Celsius. In further implementations, the first melting temperature is about 160 degrees Celsius.

In some implementations, the second temperature is between about 110 degrees Celsius and about 190 degrees Celsius. In certain implementations, the second temperature is between about 130 degrees Celsius and about 170 degrees Celsius. In further implementations, the second temperature is about 150 degrees Celsius. In some implementations, the second melting temperature is between about 130 degrees and about 210 degrees. In certain implementations, the second melting temperature is between about 150 degrees Celsius and about 190 degrees Celsius. In further implementations, the second melting temperature is about 170 degrees Celsius.

In some implementations, the third temperature is between about 110 degrees Celsius and about 190 degrees Celsius. In certain implementations, the third temperature is between about 130 degrees Celsius and about 170 degrees Celsius. In further implementations, the third temperature is about 150 degrees Celsius. In some implementations, the third melting temperature is between about 130 degrees Celsius and about 210 degrees Celsius. In certain implementations, the third melting temperature is between about 140 degrees Celsius and about 180 degrees Celsius. In further implementations, the third melting temperature is about 160 degrees Celsius. At least one advantage of the variable ranges of the first temperature, the second temperature, and the third temperature is that the temperatures can be selected to configured the sheath frame with a specific degree of penetration by the first, second, and third materials.

In some implementations, the first material, the second material, and the third material comprise at least one of polyurethane and polyether. In further implementations, at least two of the first material, the second material, and the third material are the same.

In certain implementations, the first temperature is less than at least one of the second temperature and the third temperature. In some implementations, the first temperature is less than both the second temperature and the third temperature. In certain implementations, the first temperature is less than at least one of the first melting temperature, the second melting temperature, and the third melting temperature.

In further implementations, the second temperature is less than at least one of the first melting temperature and the second melting temperature. In some implementations, the third temperature is less than at least one of the first melting temperature and the third melting temperature. In certain implementations, the first melting temperature, the second melting temperature, and the third melting temperature are substantially the same. In other implementations, only two of the first melting temperature, the second melting temperature, and the third melting temperature are substantially the same. In further implementations, none of the first melting temperature, the second melting temperature, and the third melting temperature are substantially the same. At least one advantage of the configuration of the first, second, and third temperatures to be below the first, second, and third melting points, respectively, is that the first, second, and third materials undergo an increase in tackiness upon heating without becoming liquefied by reaching their respective melting temperatures.

In some implementations, the first tackiness is greater than at least one of the second tackiness and the third tackiness. In further implementations, the first tackiness is greater than both the second tackiness and the third tackiness. In other implementations, the second tackiness is greater than at least one of the first tackiness and the third tackiness. In other implementations, the third tackiness is greater than at least one of the first tackiness and the second tackiness. In certain implementations, the first tackiness, the second tackiness, and the third tackiness are substantially the same. In other implementations, none of the first tackiness, the second tackiness, and the third tackiness are substantially the same.

In some implementations, the third depth is the width of the material that comprises the braid of the sheath assembly. In certain implementations, the first depth is less than the second depth and the third depth. In some implementations, the third depth is substantially the same as the second depth. In implementations wherein the third depth is equivalent to the width of the braid of the sheath assembly, the frame is said to be completely penetrated. At least one advantage of the complete penetration of the sheath frame by the third material is that the proximal end of the sheath assembly is prevented from buckling upon insertion of the sheath into the vasculature of the patient.

In some implementations, the first time period is between about 1 minute and about 3 minutes. In certain implementations, the first time period is about 2 minutes. In some implementations, the second time period is between about 1 minute and about 3 minutes. In further implementations, the second time period is about 2 minutes. In some implementations, the third time period is between about 1 minute and about 3 minutes. In further implementations, the third time period is about 2 minutes.

As with the relationship between the first temperature, the second temperature, the first melting temperature, and the second melting temperature, the first time period and the second time period may be selected such that the first heating and the second heating cause the first material and the second material to exhibit a desired first tackiness and a desired second tackiness, respectively. Such tackinesses provide the first material and the second material with a desired adhesion to the sheath frame. The appropriate adhesion, coupled with the desired first depth and second depth, allows the sheath to withstand forces that would otherwise lead the sheath to buckle upon insertion of the sheath into a patient without compromising the ability of the sheath to expand to accommodate pump elements having larger diameters than the sheath in an unexpanded state.

As previously discussed, the order in which the segments of the intravascular sheath are heated may be changed in order to expedite manufacturing. For example, the heating at the second temperature for the second time period may occur prior to the heating at the first temperature for the first time period. Further, the heating at the third temperature for the third time period may occur before any one of the heating at the first temperature for the first time period and the heating at the second temperature for the second time period. This advantageously allows for the manufacturing process of the sheath described herein to be easily integrated into existing manufacturing processes.

Figure 3:
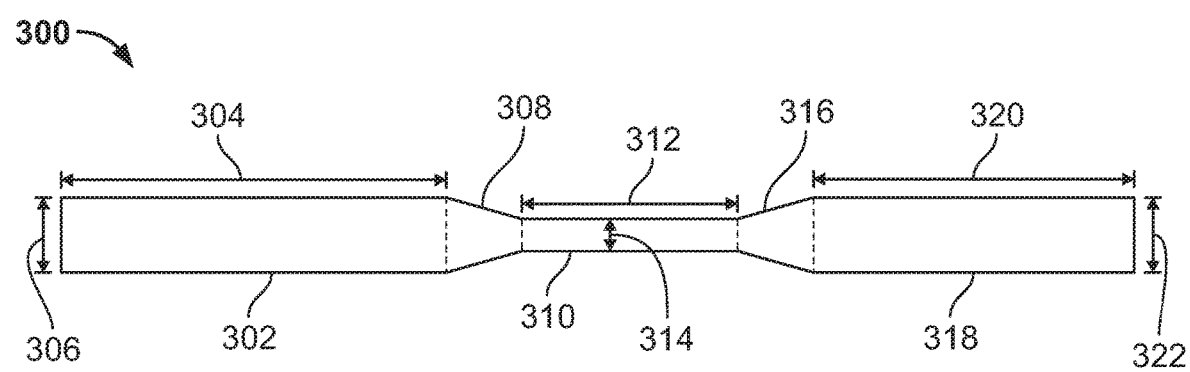
FIG. 3 shows a second illustrative mandrel.
Figure 4:
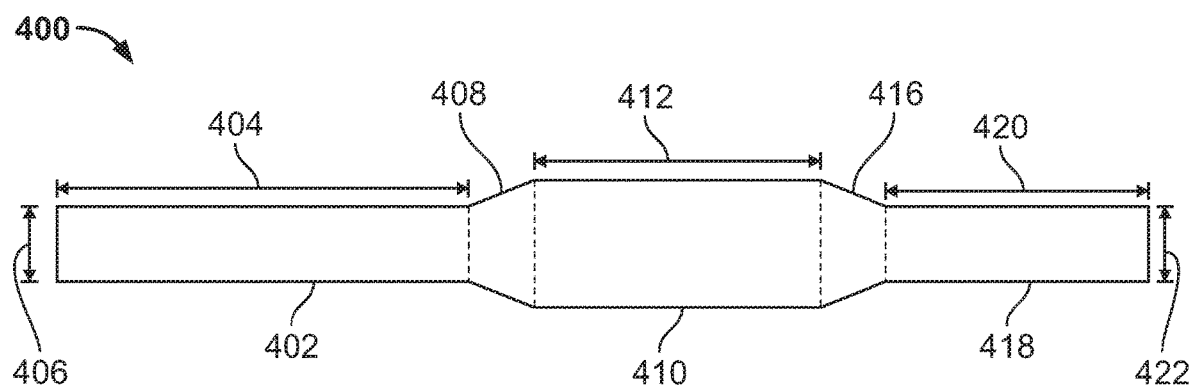
FIG. 4 shows a third illustrative mandrel.
Figure 5A:
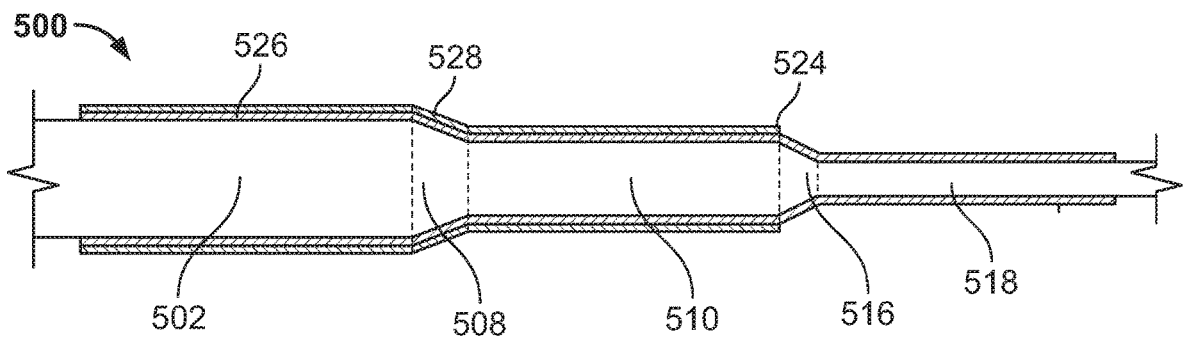
FIGS. 5A-5D shows the sheath assembly at different states of manufacturing according to the illustrative method of FIG. 1.
Figure 5B:
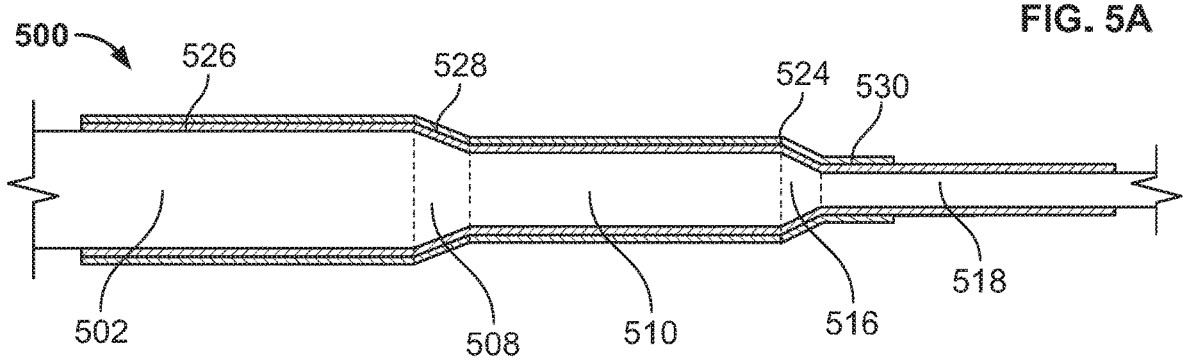
Figure 5C:
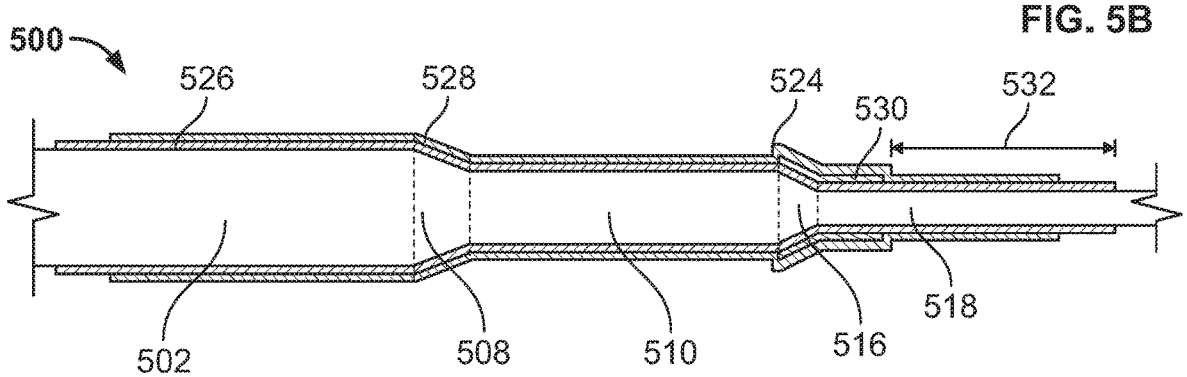
Figure 5D:
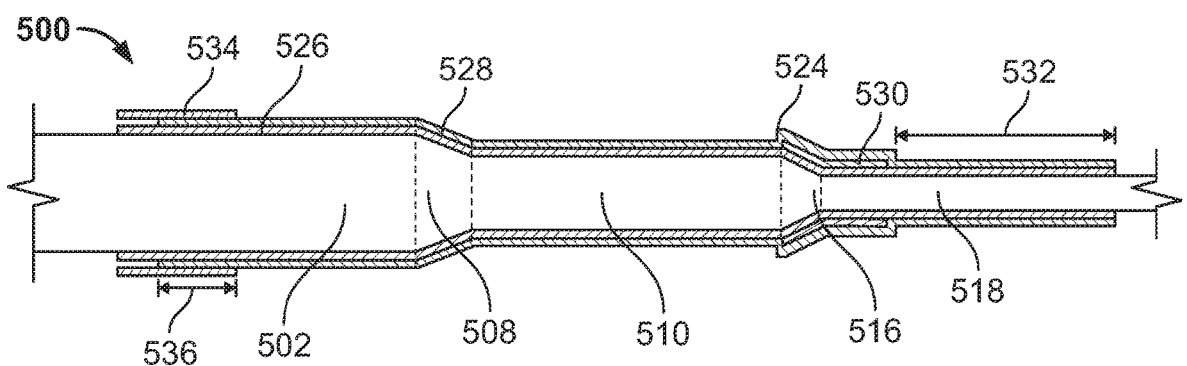

FIGS. 2, 3, and 4 show three illustrative mandrels with different geometries, for use in the method of manufacturing an expandable sheath described in FIG. 1. FIG. 2 shows a first illustrative mandrel 200 having a proximal section 202 having a first length 204 and a first diameter 206, a first transition region 208, a medial section 210 having a second length 212 and a second diameter 214, a second transition region 216, and a distal second 218 having a third length 220 and a third diameter 222. In certain implementations, proximal section 202 of mandrel 200 is cylindrical. In such implementations, mandrel 200 may have a circular cross-section. In other implementations, the cylindrical mandrel may have an elliptical cross-section. Mandrel 200, in other implementations, has a polygonal cross-section. Mandrel 200 may further comprise a free-form cross-section. The cross-section of mandrel 200 generally comprises any shape around which a sheath assembly may be placed and heated. As discussed below in relation to FIG. 5, in some implementations, a sheath assembly is placed onto proximal section 202 of mandrel 202 such that the sheath assembly covers at least proximal section 202 of mandrel 200.

In some implementations, first length 204 is between about 10 millimeters and about 20 millimeters. In certain implementations, first length 204 is between about 12 millimeters and about 18 millimeters. In further implementations, first length 204 is between about 14 millimeters and about 16 millimeters. In some implementations, first length 204 is about 15 millimeters. In some implementations, first diameter 206 is between about 2 Fr and about 6 Fr. In certain implementations, first diameter 206 is between about 3 Fr and about 5 Fr. In further implementations, first diameter 206 is about 4 Fr.

In some implementations, mandrel 200 further comprises first transition region 208 disposed distal of proximal section 202. In certain implementations, first transition region 208 has a diameter that varies over the length of first transition region 208, from the proximal end of first transition region 208 to the distal end of first transition region 208. In certain implementations, the variation in diameter of first transition region 208 is uniform along the length of first transition region 208. In other implementations, the variation in diameter of first transition region 208 is non-uniform along the length of first transition region 208. The diameter of first transition region 208 at the proximal end of first transition region 208 is equal to first diameter 206. In some implementations, the diameter of first transition region 208 decreases from first diameter 206 at the proximal end of first transition region 208 to about one half of first diameter 206 at the distal end of first transition region 208. In certain implementations, the diameter of first transition region 208 decreases from first diameter 206 at the proximal end of first transition region 208 to about three-quarters of first diameter 206 at the distal end of first transition region 208. In certain implementations, the length of first transition region 208 is between about 5 millimeters and about 15 millimeters. In further implementations, the length of first transition region 208 is between about 7 millimeters and about 13 millimeters. In certain implementations, the length of first transition region 208 is between about 9 millimeters and about 11 millimeters. In further implementations, the length of first transition region 208 is about 10 millimeters.

In further implementations, mandrel 200 further comprises medial section 210 disposed distal of first transition region 208. Medial section 210 comprises second length 212 and second diameter 214. The diameter of first transition region 208 at the distal end of first transition region 208 is equal to second diameter 214. In some implementations, second length 212 is between about 10 millimeters and about 20 millimeters. In certain implementations, second length 212 is between about 12 millimeters and about 18 millimeters. In further implementations, second length 212 is between about 14 millimeters and about 16 millimeters. In some implementations, second length 212 is about 15 millimeters. In some implementations, second diameter 214 is between about 2 Fr and about 6 Fr. In certain implementations, second diameter 214 is between about 3 Fr and about 5 Fr. In further implementations, second diameter 214 is about 4 Fr.

In some implementations, mandrel 200 further comprises second transition region 216 disposed distal of medial section 210. Similarly to first transition region 208, second transition region 216 is characterized in that the diameter of second transition region 208 varies over the length of second transition region 216, from the proximal end of second transition region 216 to the distal end of second transition region 216. In certain implementations, the variation in diameter is uniform along the length of second transition region 216. In other implementations, the variation in diameter is non-uniform along the length of second transition region 216. In some implementations, the variation in diameter of second transition region 216 is equal to the variation in diameter of first transition region 208. In other implementations, the variation in diameter of second transition region 216 is not equal to the variation in diameter of first transition region 208. The diameter of second transition region 216 at the proximal end of second transition region 216 is equal to second diameter 214. In some implementations, the diameter of second transition region 216 decreases from second diameter 214 at the proximal end of second transition region 216 to about one half of second diameter 214 at the distal end of second transition region 216. In certain implementations, the diameter of second transition region 216 decreases from second diameter 214 at the proximal end of second transition region 216 to about three-quarters of second diameter 214 at the distal end of second transition region 216.

In further implementations, mandrel 200 further comprises distal section 218 disposed distal of second transition region 216, and having third length 220 and third diameter 222. The diameter of second transition region 216 at the distal end of second transition region 216 is equal to third diameter 222. In some implementations, third length 220 is between about 10 millimeters and about 20 millimeters. In certain implementations, third length 220 is between about 12 millimeters and about 18 millimeters. In further implementations, third length 220 is between about 14 millimeters and about 16 millimeters. In some implementations, third length 220 is about 15 millimeters. In some implementations, third diameter 222 is between about 2 Fr and about 6 Fr. In certain implementations, third diameter 222 is between about 3 Fr and about 5 Fr. In further implementations, third diameter 222 is about 4 Fr.

FIG. 3 shows a second illustrative mandrel 300 having a proximal section 302 having a first length 304 and a first diameter 306, a first transition region 308, a medial section 310 having a second length 312 and a second diameter 314, a second transition region 316, and a distal second 318 having a third length 320 and a third diameter 322. In certain implementations, proximal section 302 of mandrel 300 is cylindrical. In such implementations, mandrel 300 may have a circular cross-section. In other implementations, the cylindrical mandrel may have an elliptical cross-section. In other implementations, mandrel 300 has a polygonal cross-section. In further implementations, mandrel 300 has a cross-section having a free-form shape. Generally, the cross-section of mandrel 300 is selected so that the sheath assembly can be placed and heated around mandrel 300. As discussed below in relation to FIG. 5, in some implementations, a sheath assembly is placed onto proximal section 302 of mandrel 302 such that the sheath assembly covers at least proximal section 302 of mandrel 300.

In some implementations, first length 304 is between about 10 millimeters and about 20 millimeters. In certain implementations, first length 304 is between about 12 millimeters and about 18 millimeters. In further implementations, first length 304 is between about 14 millimeters and about 16 millimeters. In some implementations, first length 304 is about 15 millimeters. In some implementations, first diameter 306 is between about 2 Fr and about 6 Fr. In certain implementations, first diameter 306 is between about 3 Fr and about 5 Fr. In further implementations, first diameter 306 is about 4 Fr.

In some implementations, mandrel 300 further comprises first transition region 308 disposed distal of proximal section 302. In certain implementations, first transition region 308 has a diameter that varies over the length of first transition region 308, from the proximal end of first transition region 308 to the distal end of first transition region 308. In certain implementations, the variation in diameter of first transition region 308 is uniform along the length of first transition region 308. In other implementations, the variation in diameter of first transition region 308 is non-uniform along the length of first transition region 308. The diameter of first transition region 308 at the proximal end of first transition region 308 is equal to first diameter 306. In some implementations, the diameter of first transition region 308 decreases from first diameter 306 at the proximal end of first transition region 308 to about one half of first diameter 306 at the distal end of first transition region 308. In certain implementations, the diameter of first transition region 308 decreases from first diameter 306 at the proximal end of first transition region 308 to about three-quarters of first diameter 306 at the distal end of first transition region 308. In certain implementations, the length of first transition region 308 is between about 5 millimeters and about 15 millimeters. In further implementations, the length of first transition region 308 is between about 7 millimeters and about 13 millimeters. In certain implementations, the length of first transition region 308 is between about 9 millimeters and about 11 millimeters. In further implementations, the length of first transition region 308 is about 10 millimeters.

In further implementations, mandrel 300 further comprises medial section 310 disposed distal of first transition region 308. Medial section 310 comprises second length 312 and second diameter 314. The diameter of first transition region 308 at the distal end of first transition region 308 is equal to second diameter 314. In some implementations, second length 312 is between about 10 millimeters and about 20 millimeters. In certain implementations, second length 312 is between about 12 millimeters and about 18 millimeters. In further implementations, second length 312 is between about 14 millimeters and about 16 millimeters. In some implementations, second length 312 is about 15 millimeters. In some implementations, second diameter 314 is between about 2 Fr and about 6 Fr. In certain implementations, second diameter 314 is between about 3 Fr and about 5 Fr. In further implementations, second diameter 314 is about 4 Fr.

In some implementations, mandrel 300 further comprises second transition region 316 disposed distal of medial section 310. Similarly to first transition region 308, second transition region 316 is characterized in that the diameter of second transition region 308 varies over the length of second transition region 316, from the proximal end of second transition region 216 to the distal end of second transition region 316. In certain implementations, the variation in diameter is uniform along the length of second transition region 316. In other implementations, the variation in diameter is non-uniform along the length of second transition region 316. In some implementations, the variation in diameter of second transition region 316 is equal to the variation in diameter of first transition region 308. In other implementations, the variation in diameter of second transition region 316 is not equal to the variation in diameter of first transition region 308. The diameter of second transition region 316 at the proximal end of second transition region 316 is equal to second diameter 314. In other implementations, the diameter of second transition region 316 increases from second diameter 314 at the proximal end of second transition region 316 to about 1.5 times second diameter 314 at the distal end of second transition region 316. In certain implementations, the diameter of second transition region 316 increases from second diameter 314 at the proximal end of second transition region 316 to about 1.25 times second diameter 314 at the distal end of second transition region 316. In certain implementations, the length of second transition region 316 is between about 5 millimeters and about 15 millimeters. In further implementations, the length of second transition region 316 is between about 7 millimeters and about 13 millimeters. In certain implementations, the length of second transition region 316 is between about 9 millimeters and about 11 millimeters. In further implementations, the length of second transition region 316 is about 10 millimeters.

In further implementations, mandrel 300 further comprises distal section 318 disposed distal of second transition region 316, and having third length 320 and third diameter 322. The diameter of second transition region 316 at the distal end of second transition region 316 is equal to third diameter 322. In some implementations, third length 320 is between about 10 millimeters and about 20 millimeters. In certain implementations, third length 320 is between about 12 millimeters and about 18 millimeters. In further implementations, third length 320 is between about 14 millimeters and about 16 millimeters. In some implementations, third length 320 is about 15 millimeters. In some implementations, third diameter 322 is between about 2 Fr and about 6 Fr. In certain implementations, third diameter 322 is between about 3 Fr and about 5 Fr. In further implementations, third diameter 322 is about 4 Fr.

FIG. 4 shows a second illustrative mandrel 400 having a proximal section 402 having a first length 404 and a first diameter 406, a first transition region 408, a medial section 410 having a second length 412 and a second diameter 414, a second transition region 416, and a distal second 418 having a third length 420 and a third diameter 422. In certain implementations, proximal section 402 of mandrel 400 is cylindrical. In such implementations, mandrel 400 may have a circular cross-section. In other implementations, the cylindrical mandrel may have an elliptical cross-section. In still other implementations, mandrel 400 comprises a polygonal cross-section. In certain implementations, mandrel 400 has a cross-section having a free-form shape. Generally, the cross-section of mandrel 400 is selected such that the sheath assembly and its components may be placed around mandrel 400 and heated. As discussed below in relation to FIG. 5, in some implementations, a sheath assembly is placed onto proximal section 402 of mandrel 402 such that the sheath assembly covers at least proximal section 402 of mandrel 400. In some implementations, first length 404 is between about 10 millimeters and about 20 millimeters. In certain implementations, first length 404 is between about 12 millimeters and about 18 millimeters. In further implementations, first length 404 is between about 14 millimeters and about 16 millimeters. In some implementations, first length 404 is about 15 millimeters. In some implementations, first diameter 406 is between about 2 Fr and about 6 Fr. In certain implementations, first diameter 406 is between about 3 Fr and about 5 Fr. In further implementations, first diameter 406 is about 4 Fr.

In some implementations, mandrel 400 further comprises first transition region 408 disposed distal of proximal section 402. In certain implementations, first transition region 408 has a diameter that varies over the length of first transition region 408, from the proximal end of first transition region 408 to the distal end of first transition region 408. In certain implementations, the variation in diameter of first transition region 408 is uniform along the length of first transition region 408. In other implementations, the variation in diameter of first transition region 408 is non-uniform along the length of first transition region 408. The diameter of first transition region 408 at the proximal end of first transition region 408 is equal to first diameter 406. In some implementations, the diameter of first transition region 408 increases from first diameter 406 at the proximal end of first transition region 408 to about 1.5 times first diameter 406 at the distal end of first transition region 408. In certain implementations, the diameter of first transition region 408 increases from first diameter 406 at the proximal end of first transition region 408 to about 1.25 times first diameter 406 at the distal end of first transition region 408.

In further implementations, mandrel 400 further comprises medial section 410 disposed distal of first transition region 408. Medial section 410 comprises second length 412 and second diameter 414. The diameter of first transition region 408 at the distal end of first transition region 408 is equal to second diameter 414. In some implementations, second length 412 is between about 10 millimeters and about 20 millimeters. In certain implementations, second length 412 is between about 12 millimeters and about 18 millimeters. In further implementations, second length 412 is between about 14 millimeters and about 16 millimeters. In some implementations, second length 412 is about 15 millimeters. In some implementations, second diameter 414 is between about 2 Fr and about 6 Fr. In certain implementations, second diameter 414 is between about 3 Fr and about 5 Fr. In further implementations, second diameter 414 is about 4 Fr.

In some implementations, mandrel 400 further comprises second transition region 416 disposed distal of medial section 410. Similarly to first transition region 408, second transition region 416 is characterized in that the diameter of second transition region 408 varies over the length of second transition region 416, from the proximal end of second transition region 416 to the distal end of second transition region 416. In certain implementations, the variation in diameter is uniform along the length of second transition region 416. In other implementations, the variation in diameter is non-uniform along the length of second transition region 416. In some implementations, the variation in diameter of second transition region 416 is equal to the variation in diameter of first transition region 408. In other implementations, the variation in diameter of second transition region 416 is not equal to the variation in diameter of first transition region 408. The diameter of second transition region 416 at the proximal end of second transition region 416 is equal to second diameter 414. In some implementations, the diameter of second transition region 416 decreases from second diameter 414 at the proximal end of second transition region 416 to about one half of second diameter 44 at the distal end of second transition region 416. In certain implementations, the diameter of second transition region 416 decreases from second diameter 414 at the proximal end of second transition region 416 to about three-quarters of second diameter 414 at the distal end of second transition region 416.

In further implementations, mandrel 400 further comprises distal section 418 disposed distal of second transition region 416, and having third length 420 and third diameter 422. The diameter of second transition region 416 at the distal end of second transition region 4 is equal to third diameter 422. In some implementations, third length 420 is between about 10 millimeters and about 20 millimeters. In certain implementations, third length 420 is between about 12 millimeters and about 18 millimeters. In further implementations, third length 420 is between about 14 millimeters and about 16 millimeters. In some implementations, third length 420 is about 15 millimeters. In some implementations, third diameter 422 is between about 2 Fr and about 6 Fr. In certain implementations, third diameter 422 is between about 3 Fr and about 5 Fr. In further implementations, third diameter 422 is about 4 Fr.

As discussed previously, the variability of the dimensions of the components of the mandrel, namely the lengths and the diameters of the mandrel sections, allows for the sheath manufactured using a given mandrel to be sized for use in a specific procedure. For example, a smaller mandrel can be used to manufacture a sheath for use in pediatric procedures, while a mandrel having larger dimensions can be used to manufacture a sheath for use in procedures performed on adult patients.

FIG. 5 illustrates the steps of the method 100 outlined in FIG. 1. In FIG. 5A, a mandrel 500 has a proximal section 502, a first transition region 508, a medial section 510, a second transition region 516, and a distal section 518. Sheath assembly 524 comprises sheath frame 526 and first sleeve 528. Sheath assembly 524 is placed onto mandrel 500. In certain implementations, sheath assembly 524 is placed onto mandrel 500 such that the distal end of sheath assembly 524 terminates in second transition region 516, and so that the proximal end of sheath assembly 524 terminates in first transition region 508. In FIG. 5B, a second sleeve 530 is placed onto distal section 518 of the mandrel. Generally, a proximal end of second sleeve 530 terminates within second transition region 516 of the mandrel. In certain implementations, such as the implementation shown in FIG. 5B, the proximal end of second sleeve 530 abuts the proximal end of second transition region 516. Second sleeve 530 comprises a second material having a second melting temperature. In FIG. 5C, first sleeve 528 is moved in the distal direction relative to sheath frame 526 and second sleeve 530 such that the distal end of first sleeve 528 overlaps with the proximal end of second sleeve 530. In some implementations, the distal end of first sleeve 528 covers second sleeve 530. In other implementations, second sleeve 530 covers the distal end of first sleeve 528. First sleeve 528 can be moved along the mandrel such that there exists length 532 between the distal end of first sleeve 528 and the distal end of second sleeve 530. In FIG. 5D, third sleeve 534 is introduced onto the distal end of sheath assembly 524. Third sleeve 534 overlaps with first sleeve 528 over length 536. In relation to method 100 of FIG. 1, FIG. 5D shows the configuration in which the sheath assembly, the second sleeve, and the third sleeve are heated at the first temperature, the second temperature, and the third temperature. At least one advantage of the variability in the relative positioning of the sleeves and the sheath frame along the mandrel is that the positions and degrees of overlap between the first, second, and third materials can be selected in order to yield a sheath with the desired material properties along its length after the sleeves are subject to the first, second, and third heatings.

The foregoing is merely illustrative of the principles of the disclosure and the apparatuses can be practiced by other than the described aspects, which are presented for purposes of illustration and not of limitation. It is to be understood that the apparatuses disclosed herein, while shown for use in percutaneous insertion of blood pumps, may be applied to apparatuses in other applications requiring optical sensors.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions and alterations are ascertainable by one skilled in the art and could be made without departing from the scope of the information disclosed herein. All references cited herein are incorporated by reference in their entirety and made part of this application.

We claim:

1. A method for manufacturing an intravascular sheath, the method comprising:
    forming a sheath assembly by:
        placing a sheath frame into a first sleeve, the first sleeve comprising a first material having a first melting temperature; and
        placing the sheath assembly onto a mandrel,
            the mandrel comprising a proximal section having a first length and a first diameter, a first transition region disposed distal of the proximal section, a medial section disposed distal of the first transition region and having a second length and a second diameter, a second transition region disposed distal of the medial section, and a distal section disposed distal of the second transition region and having a third length and a third diameter,
        wherein the sheath assembly is placed onto the mandrel so that a distal end of the sheath assembly terminates in the second transition region and the proximal end of the sheath assembly terminates in the first transition region;
    placing a second sleeve, the second sleeve comprising a second material having a second melting temperature, onto the second transition region of the mandrel such that a proximal end of the second sleeve terminates within the second transition region;
    sliding the first sleeve along the sheath frame in a distal direction so that the proximal end of the second sleeve is covered by a distal end of the first sleeve;
    placing a third sleeve, the third sleeve comprising a third material having a third melting temperature, on the proximal section of the mandrel such that a distal end of the third sleeve terminates within the proximal section of the mandrel and overlaps with a proximal portion of the sheath assembly;
    heating the sheath assembly, the second sleeve, and the third sleeve for a first time period and at a first temperature, the first temperature and the first time period being set such that after the first time period the first material, the second material, and the third material penetrate the sheath frame to a first depth;
    heating the distal end of the sheath assembly and the second sleeve for a second time period and at a second temperature, the second temperature and the second time period being set such that after the second time period the first material and the second material penetrate the sheath frame to a second depth; and
    heating the distal end of the third sleeve and the proximal portion of the sheath assembly that overlaps with the distal end of the third sleeve for a third time period and at a third temperature to form the intravascular sheath, the third temperature and the third time period being set such that after the third time period the first material and the third material penetrate the sheath frame to a third depth; and
    removing the mandrel.

2. The method of claim 1, wherein the first temperature is less than at least one of the first melting temperature, the second melting temperature, and the third melting temperature.

3. The method of claim 1, wherein the second temperature is less than at least one of the first melting temperature and the second melting temperature.

4. The method of claim 1, wherein the third temperature is less than at least one of the first melting temperature and the third melting temperature.

5. The method of claim 1, wherein the first depth is less than the second depth and the third depth.

6. The method of claim 1, wherein the second depth and the third depth are substantially the same.

7. The method of claim 1, wherein the first depth is one-half a width of a braid of the sheath frame.

8. The method of claim 1, wherein the third depth is the width of the braid of the sheath frame.

9. The method of claim 1, wherein the first temperature is between about 100 degrees Celsius and about 180 degrees Celsius.

10. The method of claim 1, wherein the first time period is between about 1 minute and about 3 minutes.

11. The method of claim 1, wherein the second temperature is between about 110 degrees Celsius and about 190 degrees Celsius.

12. The method of claim 1, wherein the second time period is between about 1 minute and about 3 minutes.

13. The method of claim 1, wherein the third temperature is between about 110 degrees Celsius and about 190 degrees Celsius.

14. The method of claim 1, wherein the third time period is between about 1 minute and about 3 minutes.

15. The method of claim 1, wherein the first length is between about one time and about 6 times at least one of the second length and the third length.

16. The method of claim 1, wherein the second length is between about one time and about 6 times at least one of the first length and the third length.

17. The method of claim 1, wherein the third length is between about one time and about 6 times at least one of the first length and the second length.

18. The method of claim 1, wherein the first diameter is between about one time and about 6 times at least one of the second diameter and the third diameter.

19. The method of claim 1, wherein the second diameter is between about one time and about 6 times at least one of the first diameter and the third diameter.

20. The method of claim 1, wherein the third diameter is between about one time and about 6 times at least one of the first diameter and the second diameter.

* * * * *

UNITED STATES PATENT AND TRADEMARK OFFICE
CERTIFICATE OF CORRECTION

| | | |
|---|---|---|
| PATENT NO. | : 11,464,963 B1 | Page 1 of 1 |
| APPLICATION NO. | : 16/552751 | |
| DATED | : October 11, 2022 | |
| INVENTOR(S) | : Robert Fishman et al. | |

It is certified that error appears in the above-identified patent and that said Letters Patent is hereby corrected as shown below:

In the Specification

Column 9, Line 34:
Now reads: "temperature temperature,"; should read --temperature,--

Column 19, Line 24:
Now reads: "of mandrel 202"; should read --of mandrel 200--

Column 20, Line 20:
Now reads: "208"; should read --216--

Column 21, Line 10:
Now reads: "of mandrel 302"; should read --of mandrel 300--

Column 22, Line 8:
Now reads: "308"; should read --316--

Column 23, Line 6:
Now reads: "of mandrel 402"; should read --of mandrel 400--

Column 23, Line 61:
Now reads: "408"; should read --416--

Signed and Sealed this
Thirty-first Day of January, 2023

Katherine Kelly Vidal
*Director of the United States Patent and Trademark Office*